United States Patent
Khoury

[19]

[11] Patent Number: 5,526,820
[45] Date of Patent: Jun. 18, 1996

[54] CATHETER WITH INTEGRAL PRESSURE SENSOR

[75] Inventor: Adib Khoury, Roswell, Ga.

[73] Assignee: Myelotec, Inc., Alpharetta, Ga.

[21] Appl. No.: 309,324

[22] Filed: Sep. 19, 1994

[51] Int. Cl.⁶ ........................................... A61B 5/00
[52] U.S. Cl. ............................................... 128/748
[58] Field of Search .................. 128/4, 748; 604/95, 604/280–283

[56] References Cited

U.S. PATENT DOCUMENTS

| | | | |
|---|---|---|---|
| 4,214,593 | 7/1980 | Imbruce et al. | 128/748 |
| 4,508,103 | 4/1985 | Calisi | 128/748 |
| 5,108,364 | 4/1992 | Takezawa et al. | 128/748 |
| 5,125,895 | 6/1992 | Buchbinder et al. | 604/95 |
| 5,168,864 | 12/1992 | Shockey | 128/4 |
| 5,218,970 | 6/1993 | Turnbull et al. | 128/748 |
| 5,308,324 | 5/1994 | Hammerslag et al. | 604/95 |
| 5,419,312 | 5/1995 | Arenberg et al. | 128/748 |
| B1 4,919,112 | 12/1993 | Siegmund | 128/4 |

FOREIGN PATENT DOCUMENTS

WO94/01162  1/1994  WIPO .

Primary Examiner—Max Hindenburg
Attorney, Agent, or Firm—Needle & Rosenberg

[57] ABSTRACT

The invention provides a pressure sensing catheter having a housing with a body portion adapted to be hand-held, a pressure sensing means situated within the catheter housing and an elongated catheter tube with a lumen extending longitudinally therethrough. The pressure sensing means has a pressure sensor element, a microprocessor and a display means located on the top surface of the catheter housing. The invention also provides a pressure sensing catheter with a steering means ergonomically adapted in a pistol-grip fashion with digitally depressible steering posts connected to steering wires for manipulating the distal end of the catheter tube. The invention also provides a pressure sensing catheter with helically braided support wires disposed along selective portions of the catheter tubing to provide differential flexibility. The invention also provided methods of using the same.

16 Claims, 2 Drawing Sheets

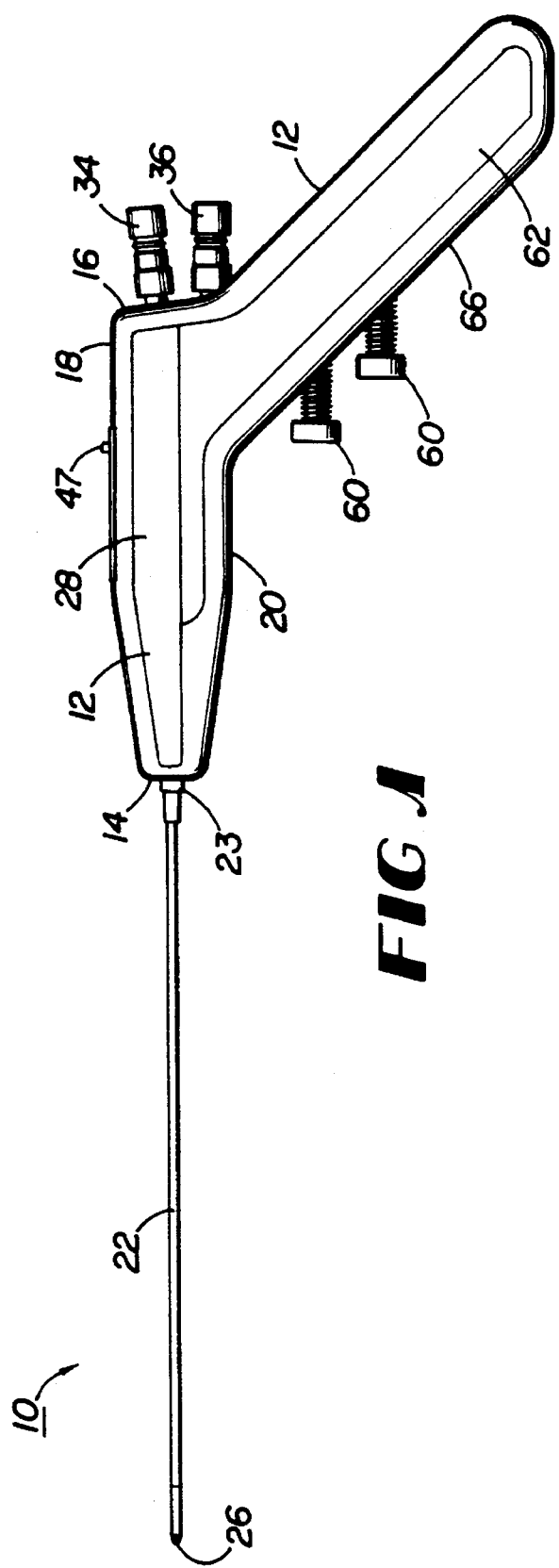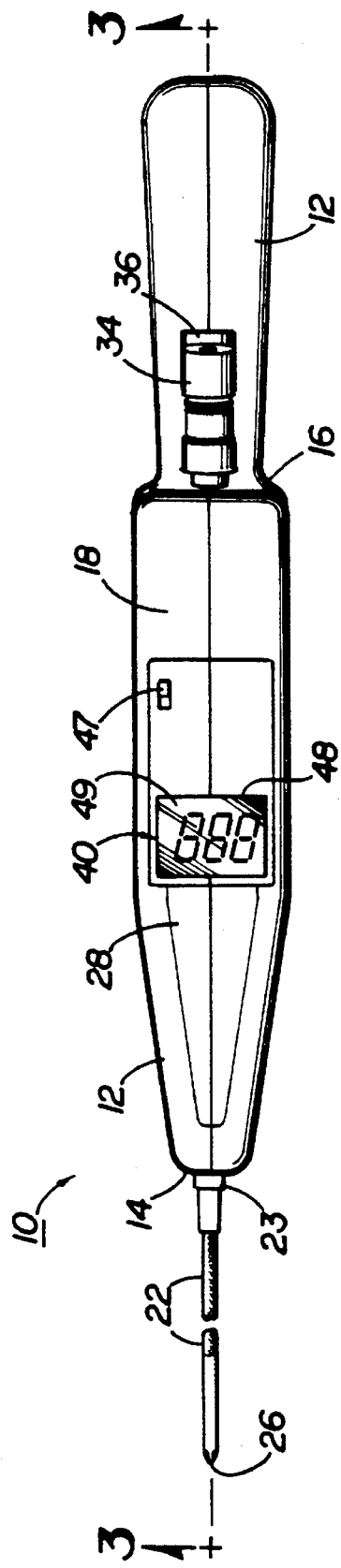

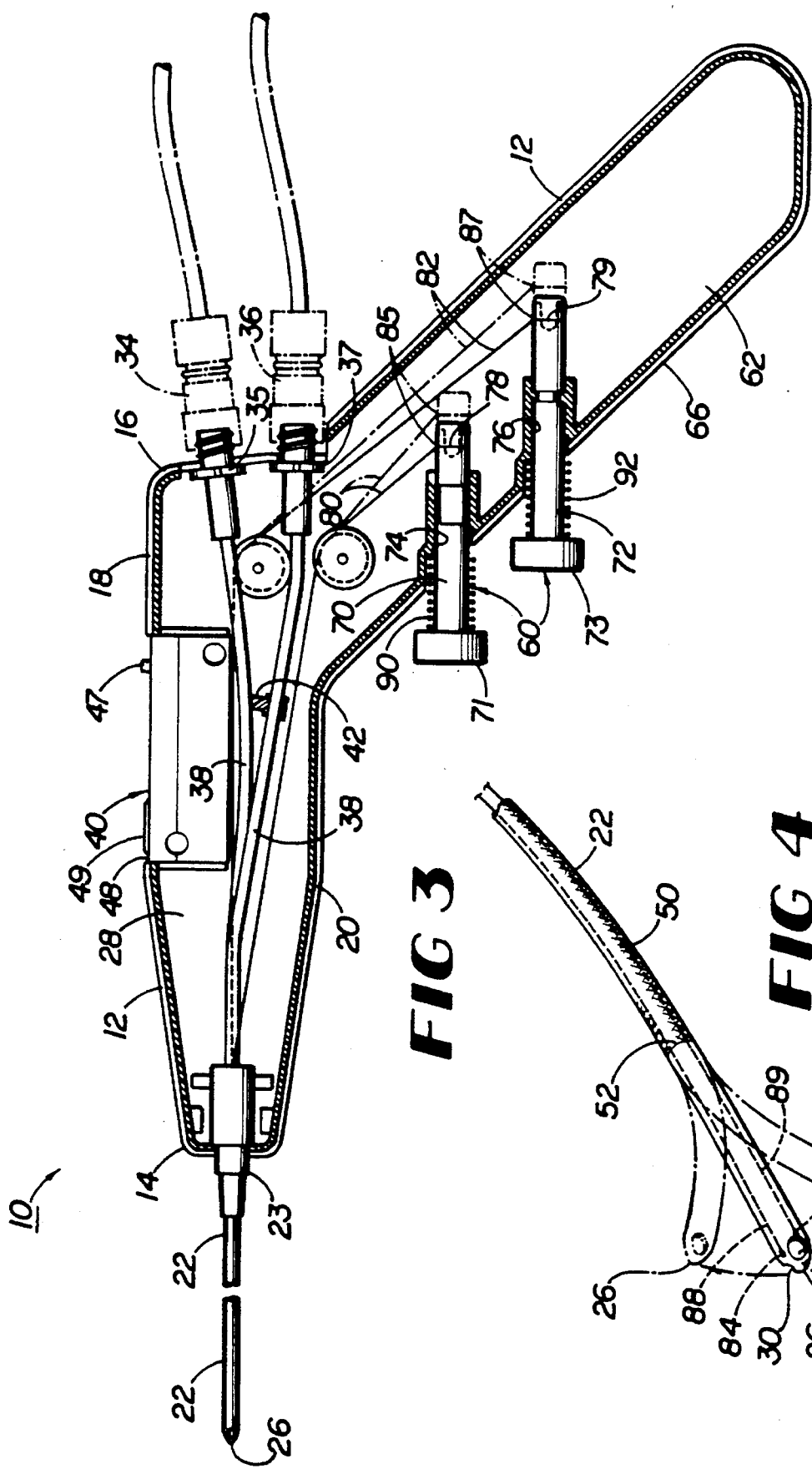

CATHETER WITH INTEGRAL PRESSURE SENSOR

FIELD OF THE INVENTION

The present invention relates to the field of medical catheters steerable for insertion into body vessels or cavities and capable of monitoring in situ fluid pressures.

BACKGROUND OF THE INVENTION

The field of medical catheters has developed to allow the minimally invasive introduction of surgical tools, diagnostic fluids, medicaments or other materials into the vessels and cavities of the body. Various catheters are commercially available which offer a variety of features, such as steering capability, multiple lumens for the insertion of surgical tools or medicaments, etc. Examples of such catheter systems may be found in U.S. Pat. No. 4,983,165 to Loiterman for "Guidance System For Vascular Catheter Or The Like," U.S. Pat. No. 4,934,340 to Ebling et al. for "Device For Guiding Medical Catheters and Scopes," and U.S. Pat. No. 4,930,521 to Metzeger et al. for "Variable Stiffness Esophageal Catheter."

An especially important feature of a catheter system is the ability to measure the internal pressure within the space in which the catheter is operating. For example, the procedure of myeloscopy requires exploring the epidural space of the spinal column. Saline is infused under pressure to enlarge the epidural space by distending the layers of tissue that cover the dura. This pressure must be carefully monitored and controlled within defined parameters for the procedure to succeed. The pressure defined by the "safety zone" minimizes venous circulation while allowing arterial circulation to continue. This prevents ischemia to the spinal tissue and avoids rupturing frail venules which otherwise cloud the field of view of the procedure.

Similarly, in a cardiac catheterization, one of the first procedures that the physician performs is to connect a remote pressure sensor to the catheter to monitor the patient's blood pressure throughout the operation. This pressure sensor detects the patient's cardiac output and after-load. The pressure reading ensures the physician that the cardiac arteries remain at a pressure within the defined "safety zone," allowing him to perform a procedure, such as angloplastic dilation, while observing and maintaining an appropriate blood pressure level.

Many commercial catheters are provided with a proximal hand-held catheter housing which contains a steering mechanism for guiding the distal end of the catheter tube with one hand. Examples of these may be seen in the PCT Patent Application No. WO 91/11213 of Lundquist et al. entitled "Catheter Steering Mechanism," European Patent Application No. 370,158 of Martin entitled "Catheter For Prolonged Access," and U.S. Pat. No. 4,737,142 to Heckele entitled "Instrument For Examination and Treatment of Bodily Passages."

A pressure sensing feature may be adapted for a catheter. The internal pressure of the vessel or cavity is sensed through the lumen of an elongated catheter tubing, extending from the distal end of the catheter to a remote pressure sensitive membrane. The pressure reading is then displayed on a large, remote monitor. This type of "closed" catheter system is useful for procedures involving a vessel or cavity with a preexisting osmotic pressure, such as for monitoring blood pressure in an angioplasty.

Catheters currently available may be constructed of an elongated polymer coated tube with at least one lumen extending longitudinally therein. In order to create a catheter possessing variable stiffness, such that the distal tip is more flexible to assist in controlling the direction of insertion, catheters may be constructed of two separate tubings of different thicknesses, which are consecutively fused together, end-to-end, at a junction.

Additionally, some catheters offer a steering mechanism which involves affixing wires within opposing lumens of the catheter and anchoring the proximal ends of the wires within the catheter housing through a pin wheel tension configuration. There are several problems presented by these present systems.

In the commonly known catheters, which are adapted to sense internal pressure, the pressure monitoring system often becomes clogged by tissues and debris, such as blood clots, or disrupted by air bubbles, because of the extensive amount of pressure tubing and numerous valves required to traverse the distance from the catheter to the remote pressure sensor and monitor. Such obstructions result in inaccurate pressure readings, which threaten the safety of the patient. Under critical cardiac operating conditions, for example, a single air bubble may cause the monitor to display very similar systolic and diastolic blood pressures, forcing the physician to terminate the procedure.

Finding the source of the disruption in pressure reading is unnecessarily difficult. The clog or air bubble could be anywhere in the extensive tubing, the remote sensor element, or in the multiple interconnecting manifolds. Since locating and removing clogs and/or air bubbles in the pressure tubing is time consuming, this greatly increases the risk of the surgical procedure for the patient.

Moreover, the remote position of the pressure monitor forces the physician to look away from the surgical field, and especially the distal end of the catheter, to check the patient's internal pressure. This further heightens the potential risks of performing a catheterization.

Additionally, it is laborious and expensive to construct the catheter tube itself by fusing together extensive polymer tubes of differing thicknesses. The spliced tube junction must align the lumens, be carefully smoothed on the outside, yet remain strong, so as to not interfere with steering the catheter into a vessel or cavity.

Furthermore, the guide wire steering mechanism of current catheter models does not provide an optimum degree of sensitivity for the control and manipulation of the catheter. The currently available steering mechanisms require the operating physician to maintain his hand in an awkward, palm-up position.

OBJECTS OF THE INVENTION

Therefore, it is an object of the present invention to provide a device with an integral pressure sensor and a digital display located within the hand-held housing at the proximal end of a catheter to allow for improved monitoring of the "safety zone" of the internal pressure at the site of operation to allow the physician to have more control over surgical catheterization procedures. It is a further object of the invention to improve the safety of the use of pressure sensing catheters and to eliminate mechanical or surgical errors due to the excessive pressure tubing currently available which may become clogged or infused with air, leading to inaccurate pressure readings.

It is also an object of the present invention to provide a catheter with a continuous catheter tubing, selectively reinforced with helically braided wires encased in a polymer, to provide variable flexibility of the catheter tube. Furthermore, it is an object of the present invention to provide a hand-held catheter with a superior guide wire steering mechanism, which is more sensitive to manipulations and is more comfortable to operate.

SUMMARY OF THE INVENTION

In accordance with the present invention, a pressure sensing catheter having a device with an integral pressure sensor and a digital display located within the hand-held housing at the proximal end of a catheter to allow for improved monitoring of the "safety zone" of the internal pressure at the site of operation to allow the physician to have more control over surgical catheterization procedures. The invention also provides a catheter with improved safety features over currently existing pressure sensing catheters which eliminates mechanical or surgical errors due to the excessive pressure tubing currently available which may become clogged or infused with air, leading to inaccurate pressure readings.

The present invention also provides a catheter with a continuous catheter tubing, selectively reinforced with helically braided wires encased in a polymer, to provide variable flexibility of the catheter tube. Additionally, the present invention provides a hand-held catheter with a superior guide wire steering mechanism. The present steering mechanism is more sensitive to the surgeon's manipulations and is ergonomically adapted to increase the surgeon's comfort.

Also provided by the present invention is a method of detecting the internal pressure of a body vessel or cavity using the improved device.

BRIEF DESCRIPTION OF THE DRAWINGS

FIG. 1 is a left side elevational view of the invention.

FIG. 2 is a top plan view of the invention.

FIG. 3 is a cut-away left side elevational view of the present invention showing the integral pressure sensing means and the steering means.

FIG. 4 is a close-up view of the distal end of the catheter tube of the present invention showing the internally embedded guide wires, two lumens and the helically braided support wires.

DETAILED DESCRIPTION OF THE INVENTION

Referring to FIGS. 1–3, the invention provides a pressure sensing catheter 10 having a housing 12 with a front end 14, a back end 16 and a top 18 and a bottom surface 20. The housing 12 is ergonomically designed to be held in the hand of the operating physician. The front end 14 of the housing 12 is connected to the proximal end 23 of a catheter tube 22. The catheter tube 22 is elongated and constructed with at least one lumen 30 (see FIGS. 4, 5) extending longitudinally therethrough. The lumen 30 provides a space for fluids under pressure to enter from the distal end 26 of the catheter tube 22. The catheter tube 22 enters the front end 14 of the housing 12 of the catheter 10 where it is attached to connector tubing 38 (see FIG. 3) extending the lumen 30 through the housing 12 interior to an access port 35 at the back end 16 of the housing 12. The access port 35 is further connected to a valve 34, such as a hemostasis valve, which permits selective access to a fluid supply tube (not shown). This type of configuration is preferred for procedures which involve the infusion of external fluids under pressure, such as in myeloscopy. After the saline solution is infused through the fluid supply tube, the valve 34 may be closed and the pressure within the closed lumen 30 and epidural space or other body cavity monitored by the pressor sensing means 40.

An alternate lumen 32 may also be equipped with an alternate access port 37 and an alternate hemostasis vane 36 that would allow the access of surgical instruments, guide wires, fiber-optic endoscopes, laser fibers, angioplasts, medicaments, etc. without a loss of internal pressure. Such instruments or medicaments then traverse through the alternate lumen 32 via the proximal end 24 of the catheter tube 22 to the distal end 26 of the catheter tube 22 to the point of internal surgery.

In the embodiment shown in FIGS. 1–3, each independent lumen 30, 32 therefore extends through the entire length of the catheter tube 22, through the respective flexible connector tubing 38, 39 to respective access ports 35, 37 and terminate in valves 34, 36, located in the back end 16 of the housing 12. Each access port 35, 37 is thus in fluid communication with the distal end 26 of the catheter tube 22 via separate respective lumen 30, 32 such that a fluid introduced into either access port 35, 37 can pass through the flexible connector tubing 38, 39, through the lumen 30, 32, and finally through the distal end 26 of the catheter tube 22.

The pressure sensing means 40 is situated in the body portion 28 of the housing 12. The pressure sensing means 40 has a pressure sensor element 42, with a diaphragm (not shown) in fluid communication with the internal pressure within the lumen 30. The pressure sensor element 42 communicates the internal pressure to a microprocessor, which interprets and relays the sensed pressure signal to a display means 48 located on the top surface 18 of the housing 12 in plain view of the operating physician.

In a preferred embodiment for a device of the present invention, the integral pressure sensing means 40 is made to the following specifications. The pressure sensing diaphragm has an operating range of 0 to 300 mmHg, and an accuracy of ±1 mmHg. The integral pressure sensing means 40 should be adapted to withstand an operating temperature of between about 10° C. to 30° C., and a storage temperature of −20° C. to 40° C.

The microprocessor analyzes the pressure signal and sends a corresponding signal to the digital display 48. A power pack (not shown) that can last for at least 5 years may be provided, although the device is expected to be used only once for approximately a 10 hour period of surgery, and then discarded. The power source is preferably a lithium battery. The pressure sensing means 40 power is controlled by an on/off switch 47 located on the top surface 18. The display means 48 has a digital display face 49 which is preferably about ½ inch by ¾ inch. The display face 49 preferably shows 3 digital numbers, with a resolution in 1 mmHg increments, through a display range of 0 to 300 mmHg. Such a pressure sensing means 40 may be obtained through custom order from Braun, Inc. (Bethlehem, Pa.).

As seen in FIG. 4, the catheter tube 22 is preferably constructed of a single elongated polymer-based tubing. The catheter tube 22 may be reinforced with helically braided wire 50 encased in the polymer along selected portions of the catheter tube 22. At the distal end 26 of the catheter tube 22, it is desirable to have more flexibility. This flexibility allows the operating physician to achieve greater steering sensitivity of the distal end 26 of the catheter tube 22. Thus, in the preferred embodiment, the reinforced braided wire 50 stops at a desired point 52 to provide a decrease in catheter rigidity. It is understood that the invention contemplates a catheter tube 22 which can have several regions of differing numbers of braided wires and differing degrees of rigidity.

The helically reinforced catheter tube 22 provides the invention with differing degrees of flexibility, with an ease of manufacturing. Many former catheters depended upon fusing together two separate catheter tubes of differing stiffness. This is a time-consuming and laborious process, because the blunt ends of the tubes must be carefully fused together by hand to preserve the continuity of the interior lumen and a smooth exterior surface. In the present invention, the catheter tube 22 may be made from a single polymer extrusion, however, the presence or absence of helically braided wires 50 embedded along its length determines the variable flexibility of the tube.

The distal end 26 of the catheter tube 22 is directed by manipulating a steering means 60. The steering means 60 has a steering grip 62 which is ergonomically shaped like a pistol-grip. The steering grip 62 has a body portion 64 with a front surface 66 and a rear surface 68 extending from the bottom surface 20 of the back end 16 of the catheter housing 12.

The steering means 60 is further equipped with a first steering post 70 and a second steering post 72. Each steering post 70, 72 has a front portion 71, 73, respectively, which is adapted for depression by the operator's fingers. The steering posts 70, 72 are each slidably disposed within a complimentary shaped channel 74, 76 which extends through the front surface 66 of the steering grip 62. A pair of first and second guide wires 80, 82 are separately attached at their respective proximal ends 85, 87 to the back portions 78, 79 of respective first and second steering posts 70, 72. The distal ends 84, 86 of the guide wires 80, 82 are separately attached to the distal end 26 of the catheter tube 22 at respective predetermined opposing points 88, 89.

Therefore, selective digital depression of either of the steering posts 70, 72 provides respectively alternating amounts of tension on said guide wires 80, 82, thereby actuating said distal end 26 of said catheter tube 22 to move in a desired direction. The catheter 10 of the present invention, thus, allows for a very sensitive and accurate steering mechanism that is controlled with minimal increments of digital deflection, and which is comfortably adapted for holding in a pistol-grip fashion.

In the preferred embodiment, the steering posts 70, 72 are each normally biased in an extended position by separate, respective biasing means 90, 92. In the embodiment shown in FIG. 3, the biasing means 90, 92 are separate coil springs disposed around respective, middle portions 75, 77 of each of the steering posts 70, 72 thereby providing a biasing force between said front portions 71, 73 of said steering posts 70, 72 and the front surface 66 of said steering grip 62, such that said each of said steering posts 70, 72 is biased in the extended position. It is understood that various biasing means 90, 92 may be configured to bias the steering posts 70, 72 in the extended position.

The present invention also provides methods of using the above-described improved device to measure the internal pressure of a body vessel or cavity. The following is provided as an outline of one example of a myeloscopic procedure utilizing the catheter 10 of the present invention with an integral pressure sensor:

1. The patient is prepared for a catheterization operation in the normal fashion.

2. An 18 Gauge touhy needle is used to access the sacrat foramen.

3. The ligamentum flavum is pierced and the needle tip is inserted in the sacrat hiatus.

5. An access sheath with a dilator in place is then threaded over the guide wire and advanced into the sacral foramen.

6. Using a turning motion, the opening is gently dilated and the dilator is advanced and sheathed into the sacral foramen.

7. The dilator is removed leaving the sheath in place.

8. This sheath is then used as an access port to introduce the catheter into the epidural space.

9. The catheter is then advanced into the ligamentum flavum and into the sacral hiatus.

10. The sheath is then removed and the catheter is threaded over the guide wire and advanced to the point being investigated.

12. The infusion port of the catheter is also coupled to the third port of the stop-cock.

13. The syringe is used first to extract all the air bubbles from the I.V. set and is then filled with normal saline to be used for distention of the epidural space.

14. As the saline is infused, the internal pressure of the epidural space is monitored by observing the digital display located on the top of the housing of the catheter. Infusion of saline continues until the internal pressure reaches approximately mean arterial pressure. The internal pressure is continually monitored by reading the digital display of the sensor means to ensure that the pressure is maintained within the safety zone range of 60–140 mmHg.

15. Approximately 100 cc's of saline will be infused into the epidural space of an adult. This amount is normally sufficient to increase the pressure in the epidural space and create a cavity in which the nerve root can be observed.

16. A flexible fiberscope is then inserted into the catheter to allow visualization of the anatomy of the epidural space.

17. The catheter is then manipulated to place the distal tip into an optimal position to avoid any adhesions or naturally occurring fat globules that could hinder the flow of drugs to the irritated nerve root.

18. Under direct visualization the catheter is manipulated until the inflammation is recognized by its redness or increased vascularity.

19. The nerve root is then examined for pathology that could be a source of irritation. Once the cause of pain or inflammation is documented, steroids are injected through the syringe port to the inflamed area.

20. The catheter is then extracted slowly and a dressing is placed at the site of entry. The patient is observed for 2 hours and discharged.

It can be appreciated that the device of the present invention can be used to monitor the pressure of any body cavity or vessel within an animal or human. The above myeloscopic procedure is in no way intended to limit the invention and is provided only as an example of one of the many uses of the device disclosed herein. The described and other features of the invention will be apparent to one with skill in the art.

What is claimed is:

1. A pressure sensing catheter comprising:

a. a housing having a body portion adapted to be hand-held;

b. a pressure sensing means situated in the body portion of said housing comprising a pressure sensor element, a microprocessor for analyzing a pressure signal from said sensor element and relaying a corresponding pressure signal to a display means visible on the housing; and, c. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element.

2. The device of claim 1, wherein said housing further comprises a front end, a back end, a top surface, a bottom surface and a plurality of individual lumen access ports located adjacent to the back end of said housing, each access port being in fluid communication with a selected one of said independent lumens.

3. The device of claim 2, wherein said lumen access ports further comprise homeostasis valves for the insertion therethrough of devices adapted for use with catheters.

4. The device of claim 1, wherein support wires are selectively helically braided together along a portion of the length of said elongated catheter tube to provide differential flexibility to said catheter tube.

5. A pressure sensing catheter comprising:
  a. a housing having a body portion adapted to be hand-held;
  b. a pressure sensing means situated in the body portion of said housing comprising a pressure sensor element, a microprocessor for analyzing a pressure signal from said sensor element and relaying a corresponding pressure signal to a display means visible on the housing;
  c. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element; and,
  d. a steering means on said hand-held housing for manipulating the direction of the distal end of said catheter tube, said steering means comprising:
    i. a steering grip having a body portion and a front surface located adjacent to the back end of said housing and extending from the bottom surface thereof,
    ii. first and second steering posts each with a from portion adapted for digital depression, a back portion and a middle portion, said steering posts being slidably disposed within a complimentary shaped channel extending through the front surface of said steering grip such that each of said front portions extends outside said steering grip, and each of said back portions extends into said body portion of said grip, and;
    iii. a pair of guide wires each with a distal end and a proximal end, the proximal ends being separately attached to said back portions of said first and second steering posts, and the distal ends being separately attached to the distal end of said catheter tube at predetermined opposing points, such that selective digital depression of either of said steering posts provides respectively alternating amounts of tension on said guide wires, thereby actuating said distal end of said catheter to move in a desired direction.

6. The device of claim 5, wherein said steering posts are each normally biased in an extended position by separate biasing means.

7. The device of claim 6, wherein said biasing means are separate coil springs disposed around said middle portion and said front portion of each of said steering posts thereby providing a biasing force between said front portion of said steering posts and said front surface of said steering grip, such that said each of said steering posts is biased in the extended position.

8. A method of determining the internal pressure of a vessel or cavity comprising:
  a. inserting a catheter into said vessel or cavity to a point where a determination of said internal pressure is desired, wherein said catheter comprises:
    i. a housing having a body portion adapted to be hand-held;
    ii. a pressure sensing means situated in the body portion of said housing comprising a pressure sensor element, a microprocessor for analyzing a pressure signal from said sensor element and relaying a corresponding pressure signal to a display means visible on the housing; and,
    iii. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element; and,
  b. determining the internal pressure at said point by reading said display means.

9. The method of claim 8, wherein said housing further comprises a front end, a back end, a top surface, a bottom surface and a plurality of individual lumen access ports located adjacent to the back end of said housing, each access port being in fluid communication with a selected one of said independent lumens.

10. The method of claim 9, wherein said lumen access ports further comprise homeostasis valves for the insertion therethrough of devices adapted for use with catheters.

11. The method of claim 8, wherein support wires are selectively helically braided together along a portion of the length of said elongated catheter tube to provide differential flexibility to said catheter tube.

12. A method of determining the internal pressure of a vessel or cavity, comprising inserting a catheter into said vessel or cavity to a point where a determination of said internal pressure is desired, wherein said catheter comprises:
  a. a housing having a body portion adapted to be hand-held;
  b. a pressure sensing means situated in the body portion of said housing comprising a pressure sensor element, a microprocessor for analyzing a pressure signal from said sensor element and relaying a corresponding pressure signal to a display means visible on the housing;
  c. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element: and,
  d. a steering means for manipulating the direction of the distal end of said catheter tube, said steering means comprising:
    i. a steering grip having a body portion and a front surface located adjacent to the back end of said housing and extending from the bottom surface thereof;

ii. first and second steering posts each with a front portion adapted for digital depression, a back portion and a middle portion, said steering posts being slidably disposed within a complimentary shaped channel extending through the front surface of said steering grip such that each of said front portions extends outside said steering grip, and each of said back portions extends into said body portion of said grip, and;

iii. a pair of guide wires each with a distal end and a proximal end, the proximal ends being separately attached to said back portions of said first and second steering posts, and the distal ends being separately attached to the distal end of said catheter tube at predetermined opposing points, such that selective digital depression of either of said steering posts provides respectively alternating amounts of tension on said guide wires, thereby actuating said distal end of said catheter to move in a desired direction; and, determining the internal pressure at said point by reading said display means.

13. The method of claim 12, wherein said steering posts are each normally biased in an extended position by separate biasing means.

14. The method of claim 13, wherein said biasing means are separate coil springs disposed around said middle portion and said front portion of each of said steering posts thereby providing a biasing force between said front portion of said steering posts and the outside of said steering grip, such that said each of said steering posts is biased in the extended position.

15. A pressure sensing catheter comprising:

a. a housing having a body portion adapted to be hand-held;

b. a pressure sensing means situated in the body portion of said housing comprising a pressure sensor element, a microprocessor for analyzing a pressure signal from said sensor element and relaying a corresponding pressure signal to a display means visible on the housing;

c. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element; and, d. a steering means on said hand-held housing for manipulating the direction of the distal end of said catheter tube.

16. A method of determining the internal pressure of a vessel or cavity comprising:

a. inserting a catheter into said vessel or cavity to a point where a determination of said internal pressure is desired, wherein said catheter comprises:

i. a housing having a body portion adapted to be hand-held;

ii. a pressure sensing means situated in the body portion of said housing comprising a pressure sensor element, a microprocessor for analyzing a pressure signal from said sensor element and relaying a corresponding pressure signal to a display means visible on the housing;

iii. an elongated catheter tube for insertion into body cavities or vessels having a proximal end connected to said housing, an opposite distal end and a plurality of independent lumens extending longitudinally therethrough such that one of said independent lumens is in fluid communication with said pressure sensor element; and, iv. a steering means on said hand-held housing for manipulating the direction of the distal end of said catheter tube; and, b. determining the internal pressure at said point by reading said display means.

* * * * *